United States Patent [19]

Ryder

[11] Patent Number: 5,320,092

[45] Date of Patent: Jun. 14, 1994

[54] FLUID DELIVERY APPARATUS WITH ALARM

[76] Inventor: Steven L. Ryder, 1334 W. Woodcrest Ave., Fullerton, Calif. 92633

[21] Appl. No.: 740,453

[22] Filed: Aug. 5, 1991

[51] Int. Cl.⁵ .......................................... A61M 16/00
[52] U.S. Cl. ........................... 128/202.22; 128/205.23; 128/205.25; 128/207.18
[58] Field of Search ...................... 128/202.22, 205.23, 128/720, 721, 206.11, 207.18, DIG. 26, 205.25

[56] References Cited

U.S. PATENT DOCUMENTS

| | | | |
|---|---|---|---|
| H1,039 | 4/1992 | Tripp, Jr. et al. | 128/202.16 |
| 3,595,228 | 7/1971 | Simon | 128/202.22 |
| 3,730,173 | 5/1973 | Deaton | 128/720 |
| 3,942,513 | 3/1976 | Frank | 128/721 |
| 4,178,932 | 12/1979 | Ryder et al. | 128/276 |
| 4,361,107 | 11/1982 | Gereg | 116/266 |
| 4,474,175 | 10/1984 | Hudimal, Jr. | 128/202.22 |
| 4,658,832 | 4/1987 | Brugnoli | 128/719 |

*Primary Examiner*—J. Reed Fisher
*Assistant Examiner*—Aaron J. Lewis
*Attorney, Agent, or Firm*—Roy A. Ekstrand

[57] ABSTRACT

An apparatus is provided for delivering a fluid to an orifice of a patient. A delivery device, such as a mask or cannula with nostril tubes, has at least one electrode for contacting with the patient's skin or other conductive surface. An alarm circuit produces an electrical alarm signal in response to an electrical condition. An electrical interconnection between each electrode and the alarm circuit is provided such that when the electrode is not in contact with the patient's skin or conductive surface the electrical condition is satisfied, thereby producing the electrical alarm signal.

11 Claims, 3 Drawing Sheets

FLUID DELIVERY APPARATUS WITH ALARM

FIELD OF THE INVENTION

This invention relates generally to fluid delivery apparati. More particularly, this invention relates to a fluid delivery apparatus, such as an oxygen mask or cannula, with an electric disconnect alarm.

BACKGROUND OF THE INVENTION

Various fluid delivery apparati, and particularly gas and aerosol delivery apparati, are well known in the medical industry. For example, the simple oxygen mask is shaped to fit around a patient's nose and mouth and is typically strapped into place with an elastic band or small tubing positioned around the patient's head. An aerosol mask is a cone-shaped shell, similar to the simple oxygen mask except that it acts as a 100 to 150 ml reservoir, has larger open ports for exhalation, and is connected to large bore tubing for higher volume flows from a nebulizer. Another type of delivery apparatus is a face mask, sometimes referred to as a face tent, which fits snugly under a patient's chin to provide aerosol to the patient's nose and mouth. This type of mask is open at the top, and can be used when the discomfort of an aerosol mask cannot be tolerated by the patient. Another type of delivery apparatus is the tracheostomy mask, which is held around the neck of the patient by an elastic band and fits directly over a stoma of the tracheotomy or the tracheostomy tube. The tubing connection of this type of mask swivels to allow for adjustment in the patient's position. Yet another type of delivery apparatus is the Briggs adaptor, also known as the T tube, which attaches directly to an endotracheal or tracheostomy tube of the patient.

It is clearly important for any type of delivery apparatus to remain positioned properly on the patient as aerosol or gas treatment of the patient it necessary. Frequently, however, due to discomfort created by such delivery apparati, a patient will often incorrectly reposition such an apparatus, or remove it altogether. Moreover, such delivery apparati may be inadvertently repositioned or removed from involuntary movement of a patient during sleep. Clearly, a nurse or respiratory practitioner should be immediately notified if such a delivery apparatus is shifted from proper placement so as to ensure that the patient is receiving the properly prescribed aerosol or gas therapy.

Several indicator devices have been used to alert medical personnel of improper conditions during a patient's gas or aerosol treatment. For example, a pressure indicating device described in U.S. Pat. No. 4,361,107 to Gereg on Nov. 30, 1982, uses a mechanical pop-out indicator to alert medical personnel of excess pressure in the delivery system. Another device taught in U.S. Pat. No. 4,474,175 to Hudimac, Jr., on Oct. 2, 1984, uses an electronic means to detect an over-abundance of nitrous oxide flowing to a patient's breathing mask. None of these devices, however, indicate when a delivery apparatus is incorrectly positioned on a patient.

Clearly there is a need for a liquid delivery apparatus that will alert health care staff of incorrect positioning of the apparatus on a patient. Such a needed device would be easy to use and monitor, and would not interfere with the delivery of the liquid to the patient. Moreover, such a needed device would be readily manufacturable in currently known delivery apparati, increasing the cost of such apparati only slightly. The present invention fulfills these needs and provides further related advantages.

SUMMARY OF THE INVENTION

The present invention is an apparatus for delivering a fluid to an orifice of a patient. A means for delivering the fluid to the orifice, such as a mask or cannula with nostril tubes, has at least one electrode means, such as an electrical conductor, for contacting a surface, such as the patient's skin. An alarm means produces an electrical alarm signal in response to an electrical condition. An electrical means for interconnection between the electrode means and the alarm means is provided such that when the electrode means is not in contact with the surface the electrical condition is satisfied, thereby producing the electrical alarm signal.

Alternative embodiments of the present invention may be used with different types of delivery means and different numbers of electrodes. For example, in the case of a cannula delivery device with nostril tubes, the at least one electrode means may be placed either on the surface of the cannula between the nostril tubes, thereby providing a contact point on the skin of the patient's nostrils, or on a delivery tube of the cannula, thereby providing a contact point on the skin of the patient's cheek. In the case where the delivery device is a face mask, the sealing edge of the face mask for contact with the patient's face includes the at least one electrode means, thereby providing a contact point on portions of the patient's face.

In the case where the delivery device is a Briggs adaptor which has a supply tube with a mounting surface, and a delivery tube with a mounting surface, at least two electrode means are fixed on the supply tube mounting surface and a conductor is fixed onto the mounting surface of the delivery tube. With such a Briggs adaptor, when the supply tube is fully mounted to the delivery tube, the conductor of the delivery tube is in contact with the electrodes of the supply tube, closing the circuit between the at least two electrodes.

In the case where the delivery device is either the cannula with nostril tubes or a face mask, one, two, or more electrode means may be used. In the case where one electrode means is used, the alarm means detects when the electrode means is in contact with a person's skin, sounding the alarm if the contact between the electrode means and the person's skin is broken. In the case where two or more electrode means are used, the alarm means determines if either of the two electrodes are removed from contact with the patient's skin, whereby the circuit between the two electrodes is broken and the resistance between the two electrodes significantly increases.

In operation, the delivery device is properly fitted to the patient and the aerosol treatment is begun. Then the alarm means is activated, the alarm means monitoring the electrical condition of the at least one electrode means. If the delivery device is shifted from its proper position such that the electrical condition is satisfied, the alarm means activates an electronic alarm signal, alerting a health care staff and/or the patient that the delivery device should be properly repositioned. Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 2:
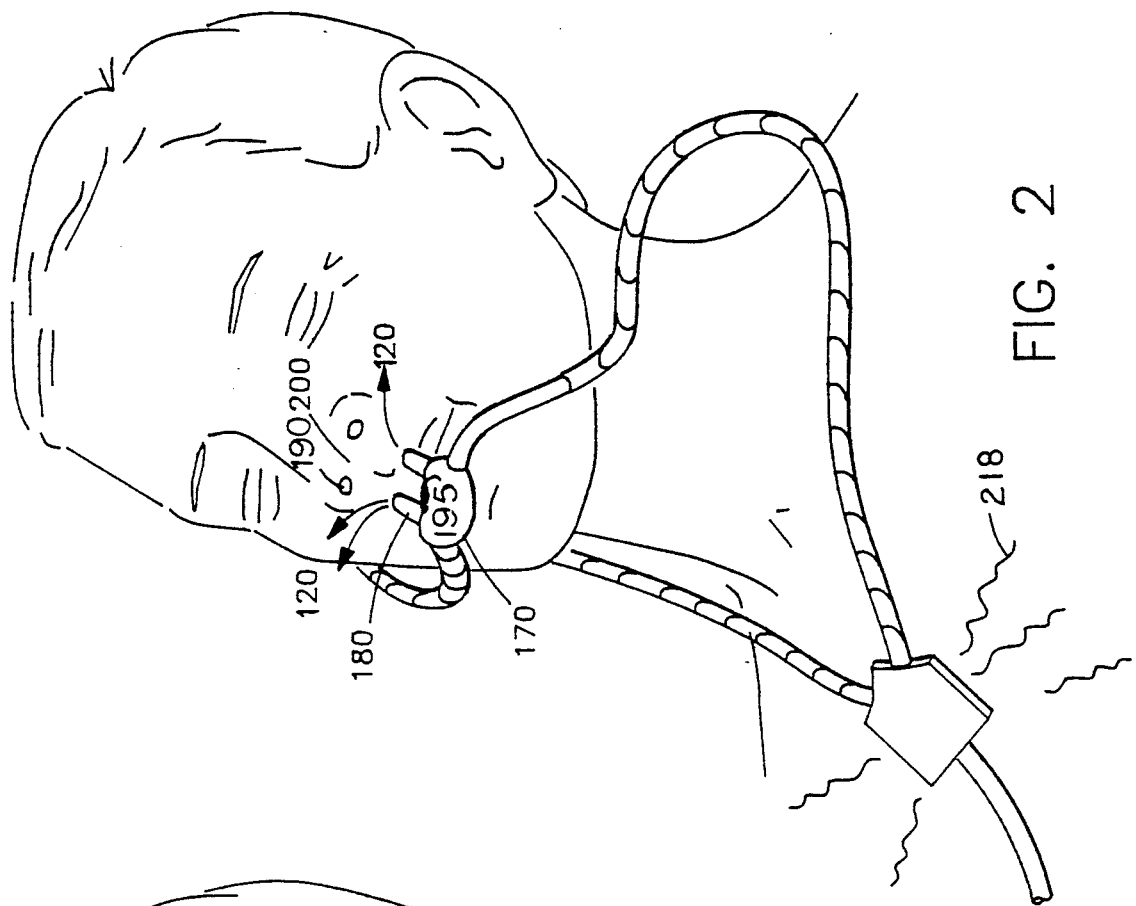
FIG. 2 is a perspective view of the invention of FIG. 1, showing the cannula not properly fitted to the patient.
Figure 1:
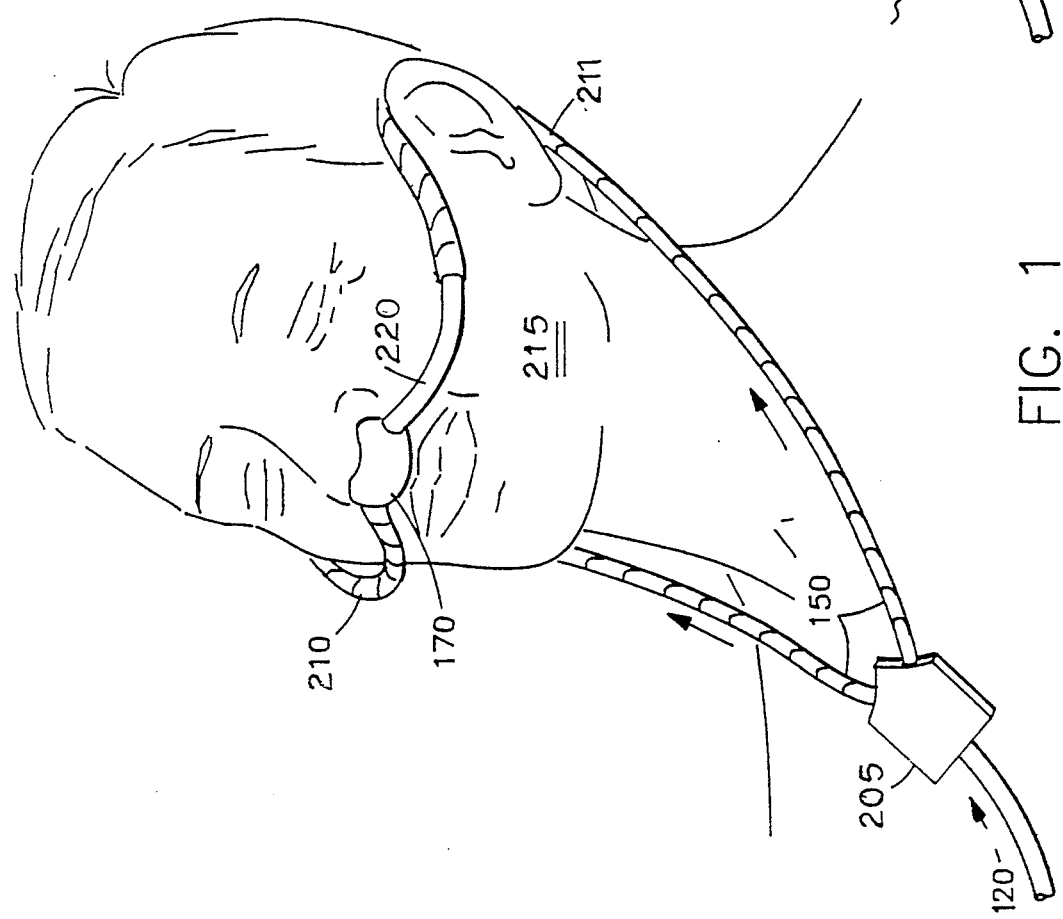
FIG. 1 is a perspective view of the invention embodied in a cannula and as worn by a patient, illustrating electrode means in contact with the patient's skin at the nostrils and cheek.

FIG. 1 illustrates an apparatus for delivering a fluid 120 such as oxygen or other gas to a patient during normal inhalation therapy. A delivery means 150, such as a flexible plastic tube provides a means of continuous supply of the fluid 120 from a source located near the bedside to a cannula 170 (FIGS. 1 and 2). Cannula 170 is designed for insertion into the patient's nose so that it has two nostril pipes 180 for inserting into the nostrils 30 whereby a first electrode 60 which is located on the exterior surface of the cannula 170 between the two nostril pipes 180 forms an electrical contact with that portion of the nose surface 200 which lies between the nostrils 190 when the nostril pipes 180 are fully inserted into the nostrils 190. The first electrode 195 is electrically interconnected with an alarm circuit located within alarm means 205 by a non-exposed electrically conductive path 210 on delivery means 150. An exposed electrically conductive path 211 forms a second electrode in contact with the skin surface 215 at any point or points near the cheek or ear area of the patient's face and is electrically interconnected with the alarm circuit within alarm means 205 via delivery means 150. In this configuration the alarm circuit senses the level of resistance between the first and the second electrodes 195, 211. When this resistance is relatively low, i.e., the skin resistance between these two points, which might be between some tens of ohms and several megohms depending upon the condition of the skin, the alarm is not triggered. When, however, the cannula 170 is not in its proper place, the first electrode 195 is not in contact with the nose and resistance between these points rises to hundreds of megohms so that an open circuit condition is indicated and alarm means 205 produces an electrical alarm signal 218 in response. Various possibilities exist for fabricating the electrical paths 210 and 211. These paths may be wires, foils, plated surfaces or deposited surfaces. One inexpensive method of fabricating these path is to deposit an allow such as indium tin onto the tubing of delivery means 150 while assuring that a non-coated portion 220 separates cannula 170 and path 211. To assure that path 210 is not exposed a further coating of an insulating material such as silicon dioxide may be deposited over path 210. These deposits may be made quite thin so that they are highly flexible with the tubing and also invisible to the eye. Films such as these have been successfully made using any one of a variety of sputtering processes.

Figure 4:
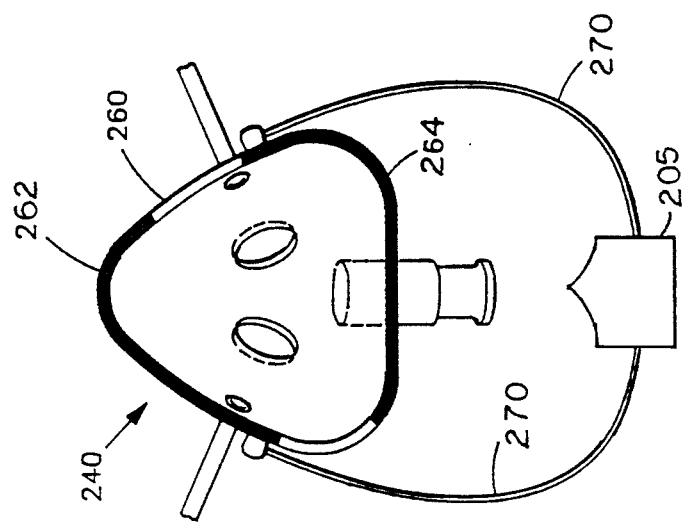
FIG. 4 is a rear elevational view of the invention, taken generally along lines 4—4 of FIG. 3, illustrating electrodes at a sealing edge of the mask.
Figure 3:
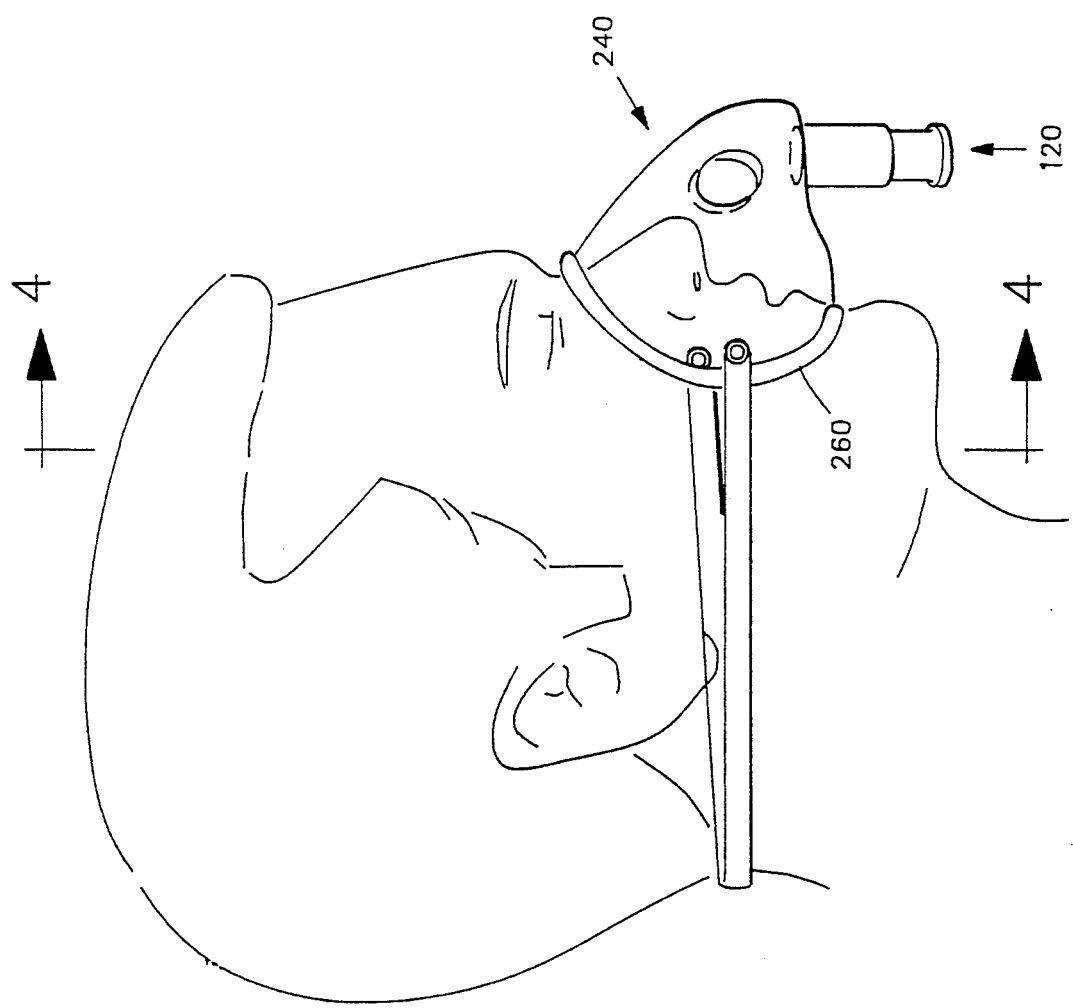
FIG. 3 is a right side elevational view of the invention embodied in a face mask as worn by a patient.

In one alternate embodiment shown in FIG. 3 and FIG. 4 a breathing mask 240 replaces the cannula 170. The opening 260 of the mask 240 fits tightly against the skin surface 215 of the patient's face so that electrodes 262, 264 are in direct contact with the skin surface 215. Alarm means 205 is interconnected to electrodes 262, 264 via wires 270 so that if the mask looses contact with the face of the patient, the alarm is triggered.

Figure 6:
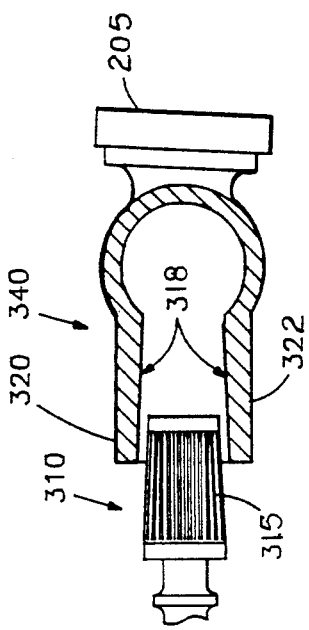
FIG. 6 is a cross-sectional view of the invention, taken generally along lines 6—6 of FIG. 5.
Figure 5:
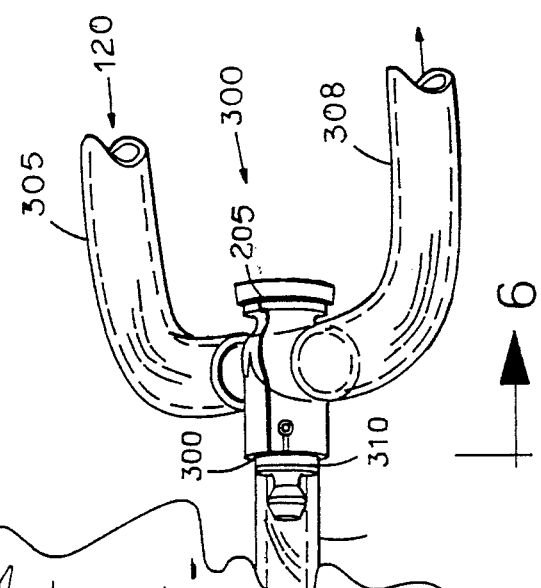
FIG. 5 is a right side elevation view of the invention embodied in a Briggs adaptor as worn by a patient, illustrating electrodes in contact with a conductor at mounting surfaces of a supply tube and a delivery tube.
Figure 5:
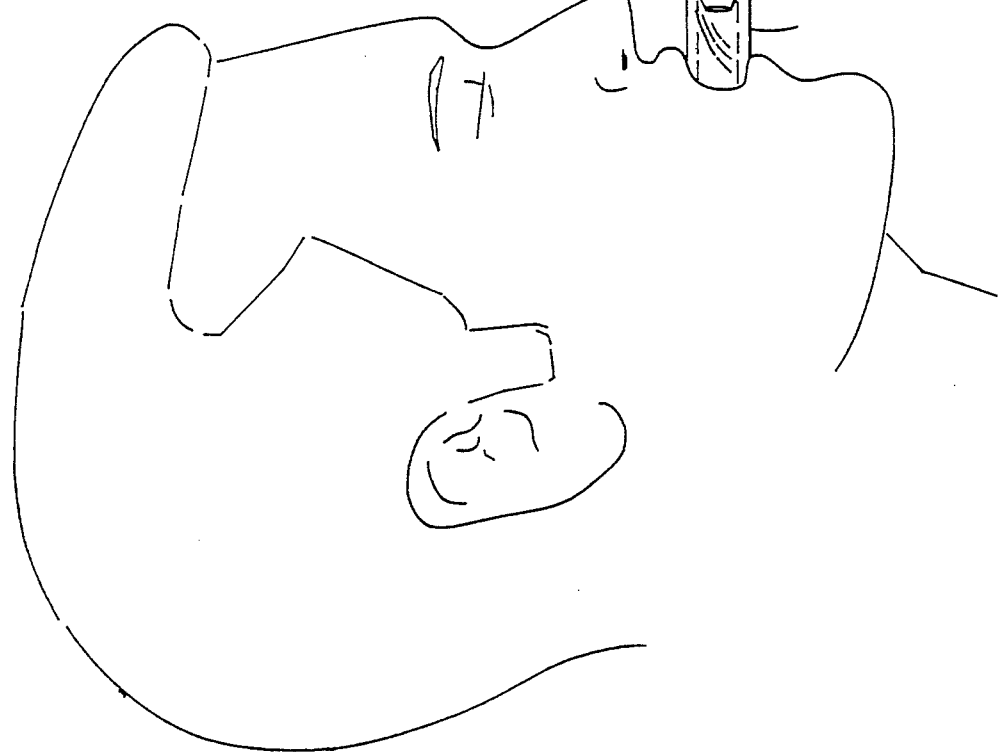

In a further embodiment as shown in FIG. 5, a "T" or "Y" shaped sensor tube 300 has attached thereto a supply tube 305, an exit tube 308 and a delivery tube 309. The delivery tube 309 is inserted into the mouth or the tracheostomy of a patient. The supply tube 305 provides a constant flow of the fluid 120 which enters the sensor tube 340 and thereby flows into the delivery tube 390 to the patient. Excess fluid 120 flows out of the exit tube 308. The exterior portion of the delivery tube terminates in an adaptor 310 for attachment by friction fit to the sensor tube 300. The adaptor external surface 330 is electrically conductive as is the mating sensor tube internal surface 340. As shown in FIG. 6, surface 340 is partitioned into two mutually isolated conductors 320, 322. When the adaptor 310 is inserted into the sensor tube 300, surface 330 makes electrical contact with both conductors 320 and 322 so they become electrically common.

Conductors 320 and 322 are individually routed to alarm means 205 which is mounted externally on the sensor tube 300. The breaking of the connection between electrodes 320 and 322 is used to trigger alarm means 205 for warning that the gas flow to the patient may have been interrupted.

In operation, the delivery device is fitted to the patient. The alarm means 205 is activated and sounds the alarm signal if the delivery device is not properly fitted to the patient. Should the delivery device shift from a proper position on the skin surface 215 of the patient, the alarm signal will sound, alerting the patient or health care staff that the delivery device is incorrectly positioned and in need of adjustment. A delay button (not shown) may be included to temporarily disable the alarm means 205 so that correct positioning of the delivery device may be effected without the alarm signal sounding. A permanent disable switch is excluded from the preferred embodiment, thereby preventing the patient from disabling the alarm himself.

While the invention has been described with reference to a few preferred embodiments, it is to be clearly understood by those skilled in the art that the invention is not limited thereto. For example, anyone skilled in the art would be able to manufacture an apparatus using a variety of delivery means 150 and a variety of electrode means without changing the spirit and scope of the present invention. Moreover, any such apparatus may be easily manufactured with one, two, or more electrode means as herein described. In addition, the alarm means 205 may be a simple apparatus included within the structure of the delivery means 150, or part of a larger monitoring apparatus (not shown) that monitors several patients simultaneously. Thus, the scope of the invention is to be interpreted only in conjunction with the appended claims.

I claim:

1. An apparatus for delivering a fluid to an orifice of a patient having a skin surface adjacent said orifice, the apparatus comprising:
   means for the delivery of the fluid to the orifice having a fluid delivery pipe insertable into said orifice and having a skin contacting portion having at least one electrode supported thereon for electrically contacting at least a portion of said skin surface, said electrode being positioned to contact said skin surface adjacent said orifice responsive to said delivery pipe being inserted into said orifice;
   alarm means producing an alarm signal in response to an electrical condition;
   a non-exposed electrically conductive path interconnecting the at least one electrode and the alarm means such that when the at least one electrode is not in contact with said skin surface the electrical condition is satisfied thereby producing the alarm signal.

2. The apparatus of claim 1 wherein the conductive path containing the elements indium and tin.

3. The apparatus of claim 2 wherein the conductive path is a deposited thin film formed by a sputtering process.

4. An apparatus for delivering a fluid to an orifice of a patient, the patient having a skin surface surrounding said orifice, the apparatus comprising:
   means for delivery of the fluid to the orifice having a delivery pipe and having a skin contacting portion contacting said skin surface when said delivery pipe is coupled to said orifice;
   at least one electrode supported upon said skin contacting portion for contacting the skin surface, the electrode resting against the skin surface solely when said means for delivery and said delivery pipe are coupled to said orifice;
   alarm means for producing an alarm signal in response to an electrical condition;
   electrical means interconnecting the at least one electrode means and the alarm means such that when the at least one electrode means is not in contact with the skin surface due to said means for delivery being moved such that the coupling of said delivery pipe to said orifice is disturbed, the electrical condition is satisfied thereby producing the electrical alarm signal.

5. The apparatus of claim 4 wherein said means for delivery includes a cannula having a pair of nostril tubes, wherein the at least one electrode means is an electrical conductor on the surface of the cannula positioned between the pair of nostril tubes, the conductor being in contact with a portion of the skin surface.

6. The apparatus of claim 5 further including a second electrode in contact with a second portion of the skin surface, such that the skin resistance between the at least one electrode and the second electrode is less than at open circuit.

7. The apparatus of claim 5 wherein the electrical condition is measured by the capacitance between the at least one electrode and ground.

8. The apparatus of claim 4 wherein said means for delivery includes a face mask having an opening for contact with the skin surface, wherein the at least one electrode means is an electrical conductor on the opening.

9. The apparatus of claim 8 further including a second electrode in contact with a second portion of the skin surface, such that the skin resistance between the at least one electrode and the second electrode is less than at open circuit.

10. The apparatus of claim 8 wherein the electrical condition is a measure of the capacitance between the at least one electrode and ground.

11. For use in delivery of a fluid to a patient orifice having a skin surface proximate said orifice, fluid delivery apparatus comprising:
    means for coupling a source of to-be-delivered fluid to said patient orifice having a skin surface contacting portion contacting said skin surface proximate said orifice during fluid delivery;
    an electrical contact supported upon said skin contacting portion of said means for coupling touching said skin surface proximate said orifice when said means for coupling is coupled to said patient orifice;
    alarm means for producing an alert signal; and
    connection means electrically connecting said alarm means to said electrical contact,
    said alarm means responsive to an electrical condition caused by separation of said electrical contact from said skin surface proximate said orifice when said means for delivery is not coupled to said orifice to produce said alert signal and indicate disturbance of said means for coupling from said orifice.

* * * * *